United States Patent [19]
Bolton et al.

[11] Patent Number: 5,571,792
[45] Date of Patent: Nov. 5, 1996

[54] HISTIDINE AND HOMOHISTIDINE DERIVATIVES AS INHIBITORS OF PROTEIN FARNESYLTRANSFERASE

[75] Inventors: Gary L. Bolton; John C. Hodges; Michael W. Wilson, all of Ann Arbor, Mich.

[73] Assignee: Warner-Lambert Company, Morris Plains, N.J.

[21] Appl. No.: 268,364

[22] Filed: Jun. 30, 1994

[51] Int. Cl.$^6$ ............... A61K 31/415; C07D 233/64; C07K 5/078; C07K 5/097

[52] U.S. Cl. ............... 514/18; 514/19; 514/94; 514/311; 514/399; 546/146; 548/111; 548/338.1; 530/331

[58] Field of Search ............... 514/18–19, 94, 514/311, 399; 530/330–331; 548/111, 338.1; 546/146

[56] References Cited

U.S. PATENT DOCUMENTS

| | | | |
|---|---|---|---|
| 5,260,276 | 11/1993 | Cody et al. | 530/331 |
| 5,464,820 | 11/1995 | Burton et al. | 530/331 |

FOREIGN PATENT DOCUMENTS

| | | |
|---|---|---|
| 0461869 | 12/1991 | European Pat. Off. |
| 0520823 | 12/1992 | European Pat. Off. |
| 0523873 | 1/1993 | European Pat. Off. |
| 0528486 | 2/1993 | European Pat. Off. |
| 0535730 | 4/1993 | European Pat. Off. |
| 9116340 | 10/1991 | WIPO |
| 9400419 | 1/1994 | WIPO |
| 9509001 | 4/1995 | WIPO |

OTHER PUBLICATIONS

Leftheris, et al., *Bioorganic & Medicinal Chemistry Letters*, vol. 4, No. 7, pp. 887–892 (1994).
PCT Search /report PCT/US95/06660 (Sep. 1995).
*Cell*, vol. 65, pp. 1–4 (1991), Gibbs, J. B.
*Chimicaoggi*, Mar. 1992, pp. 26–33, Cartwright et al.
*Microbiological Reviews*, vol. 55, No. 2, pp. 171–185 (1989), Gibbs et al.
*Hypertension*, vol. 13, pp. 706–711 (1989), Naftilan et al.
*J. Clin. Invest.*, vol. 83, Apr. 1989, pp. 1419–1424, Naftilan et al.
*Hypertension*, vol. 14, No. 3, p. 358 (1989), Gibbons et al. abstract.
*Molecular and Cellular Biology*, vol. 13, No. 6, pp. 3706–3713 (1993), Satoh et al.
*Cell*, vol. 57, pp. 1167–1177 (1989), Hancock et al.
*Science*, vol. 245, pp. 379–385 (1989), Schafer et al.
*Proc. Natl. Acad. Sci. USA*, vol. 86, pp. 8323–8327 (1989), Casey et al.
*Biochem. Soc. Trans.*, vol. 20, pp. 487–488 (1992), Reiss et al.
*J. Biol. Chem.*, vol. 268, No. 13, pp. 9675–9680 (1993), Chen et al.
*Science*, vol. 260, pp. 1934–1937 (1993), Kohl et al.
*Science*, vol. 260, pp. 1937–1942 (1993), James et al.
*J. Biol. Chem.*, vol. 268, No. 25, pp. 18415–198418 (1993), Garcia et al.

*Primary Examiner*—Jeffrey E. Russel
*Attorney, Agent, or Firm*—Charles W. Ashbrook; Todd M. Crissey

[57] ABSTRACT

Novel inhibitors of protein farnesyltransferase enzyme are described, as well as methods for the preparation and pharmaceutical compositions of the same, which are useful in controlling tissue proliferative diseases, including cancer and restenosis.

19 Claims, No Drawings

HISTIDINE AND HOMOHISTIDINE DERIVATIVES AS INHIBITORS OF PROTEIN FARNESYLTRANSFERASE

FIELD OF THE INVENTION

The present invention pertains to a number of compounds which can be used in the medicinal field to treat, prophylactically or otherwise, uncontrolled or abnormal proliferation of human tissues. More specifically, the present invention pertains to a number of compounds which act to inhibit the farnesyltransferase enzyme that has been determined to activate ras proteins which in turn activate cellular division and are implicated in cancer and restenosis.

BACKGROUND OF THE INVENTION

Ras protein (or p21) has been examined extensively because mutant forms are found in 20% of most types of human cancer and greater than 50% of colon and pancreatic carcinomas (Gibbs J. B., *Cell*, 65:1 (1991), Cartwright T., et al., *Chimica. Oggi.*, 10:26 (1992)). These mutant ras proteins are deficient in the capability for feedback regulation that is present in native ras and this deficiency is associated with their oncogenic action since the ability to stimulate normal cell division can not be controlled by the normal endogenous regulatory cofactors. The recent discovery that the transforming activity of mutant ras is critically dependent on post-translational modifications (Gibbs J., et al., *Microbiol. Rev.*, 53:171 (1989)) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy and transluminal coronary angioplasty is often accompanied by complications due to uncontrolled growth of neointimal tissue, known as restenosis. The biochemical causes of restenosis are poorly understood and numerous growth factors and protooncoggenes have been implicated (Naftilan A. J., et al., *Hypertension*, 13:706 (1989) and *J. Clin. Invest.*, 83:1419; Gibbons G. H., et al., *Hypertension*, 14:358 (1989); Satoh T., et al., *Mollec. Cell. Biol.*, 13:3706 (1993)). The fact that ras proteins are known to be involved in cell division processes makes them a candidate for intervention in many situations where cells that are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyltransferase (PFT). This consensus sequence consists of a cysteine residue located four amino acids from the carboxyl terminus, followed by two lipophilic amino acids and the C-terminal residue. The sulfhydryl group of the cysteine residue is alkylated by farnesylpyrophosphate in a reaction that is catalyzed by protein farnesyltransferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., *Cell*, 57:1167 (1989), Schafer W. R., et al., *Science*, 245:379 (1989), Casey P. J., *Proc. Natl. Acad. Sci. USA*, 86:8323 (1989)).

Recently, protein farnesyltransferases (PFTs), also referred to as farnesyl proteintransferases (FPTs) have been identified and a specific PFT from rat brain was purified to homogeneity (Reiss Y., et al., *Bioch. Soc. Trans.*, 20:487–88 (1992)). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W. -J., et al., *J. Biol. Chem.*, 268:9675 (1993)).

In light of the foregoing, the discovery that the function of oncogenic ras proteins is critically dependent on their post-translational processing provides a means of cancer chemotherapy through inhibition of the processing enzymes. The identification and isolation of a protein farnesyltransferase that catalyzes the addition of a farnesyl group to ras proteins provides a promising target for such intervention. Recently, it has been determined that prototypical inhibitors of PFT can inhibit ras processing and reverse cancerous morphology in tumor cell models (Kohl N. E., et al., *Science*, 260:1934 (1993), James G. L., et al., *Science*, 260:1937 (1993), Garcia A. M., et al., *J. Biol. Chem.*, 268:18415 (1993)). Thus, it is possible to prevent or delay the onset of cellular proliferation in cancers that exhibit mutant ras proteins by blocking PFT. By analogous logic, inhibition of PFT would provide a potential means for controlling cellular proliferation associated with restenosis, especially in those cases wherein the expression and/or function of native ras is overstimulated.

SUMMARY OF THE INVENTION

Accordingly, the present invention is a histidine or homohistidine derivative of Formula I,

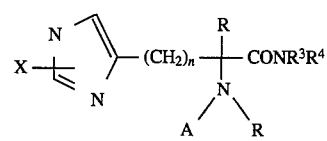

wherein:

n=1 or 2;

A=$COR^2$, $CO_2R^2$, $CONHR^2$, $CSR^2$, $C(S)OR^2$, $C(S)NHR^2$, or $SO_2R^2$ with $R^2$ as defined below;

R=independently H or Me;

$R^2$=alkyl, $(CH_2)_m$-cycloalkyl, $(CH_2)_m$-aryl, $(CH_2)_m$-heteroaryl with m=0, 1, 2, or 3;

$R^3$ and $R^4$=independently

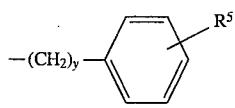

or $(CH_2)_n CONH-R^6$ with y=1–5 and n as defined above and with $R^5$ and $R^6$ as defined below, or $R^3$ and $R^4$ are connected together to form a ring of the following type:

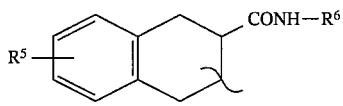

with $R^5$ and $R^6$ as defined below, or $(CH_2)-R^7$, with x=2–5, and $R^7$ as defined below;

$R^5=R^2$, $OR^2$, or $SR^2$ with $R^2$ as defined above;

$R^6=(CH_2)_n R^5$, $(CH_2)_n CO_2 R^2$, $(CH_2)_n CONHR^2$, $(CH_2)_n CONH(CH_2)_{n+1} R^5$, $CH(COR^8)$ $(CH_2)_n R^5$, with n, $R^2$, and $R^5$ as defined above and $R^8$ as defined below;

$R^7=(CH_2)_m$-cycloalkyl, $(CH_2)_m$-aryl, $(CH_2)_m$-heteroaryl, $O(CH_2)_m$-cycloalkyl, $O(CH_2)_m$-aryl, $O(CH_2)_m$-heteroaryl with m=0, 1, 2, or 3;

$R^8$=OH, O-alkyl, $NH_2$, or NH-alkyl; and

X=H, Me, $(CH_2)_n CO_2 R^9$, or $(CH_2)_n P(O)(OR^9)_2$, with $R^9$=H or alkyl;

or a pharmaceutically acceptable salt thereof.

The present invention is also directed to the use of a compound of Formula I, or a pharmaceutically acceptable salt thereof, to inhibit the activity of a protein farnesyltransferase enzyme as a method for treating tissue proliferative diseases.

A further embodiment of the present invention is the use of a pharmaceutical composition including a therapeutically effective amount of Formula I, or a pharmaceutically acceptable salt thereof, as a method for the treatment of cancer.

A still further embodiment of the present invention is the use of a pharmaceutical composition including a therapeutically effective amount of Formula I, or a pharmaceutically acceptable salt thereof, as a method for the treatment of restenosis.

A still further embodiment of the present invention is a pharmaceutical composition for administering a therapeutically effective amount of a compound of Formula I, or a pharmaceutically acceptable salt thereof, in unit dosage form in the treatment methods mentioned above.

A final embodiment of the present invention pertains to methods for the preparation of compounds of Formula I, or pharmaceutically acceptable salts thereof, by solid phase synthesis, solution phase synthesis, and simultaneous multiple syntheses using a "DIVERSOMER™" (multiple simultaneous solid phase synthesis) apparatus.

DETAILED DESCRIPTION OF THE PREFERRED EMBODIMENTS

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, Cl, Br, I, $CF_3$, $NO_2$, $NH_2$, $NHCH_3$, $N(CH_3)_2$, NHCO-alkyl, $(CH_2)_m CO_2 H$, $(CH_2)_m CO_2$-alkyl, $(CH_2)_m SO_3 H$, $(CH_2)_m PO_3 H_2$, $(CH_2)_m PO_3(alkyl)_2$, $(CH_2)_m SO_2 NH_2$, and $(CH_2)_m SO_2 NH$-alkyl wherein alkyl is defined as above and m=0, 1, 2, or 3.

The term "heteroaryl" means a heteroaromatic ring which is a 2- or 3-thienyl, 2- or 3-furanyl, 2- or 3-pyrrolyl, 2-, 3-, or 4-pyridyl, 2-, 3-, 4-, 5-, 6-, or 7-indolyl group, substituted or unsubstituted by 1 or 2 substituents from the group of substituents described above for aryl.

The following table provides a list of abbreviations and definitions thereof used in the present invention.

| TABLE OF ABBREVIATIONS | |
| --- | --- |
| Abbreviation* | Amino Acid |
| Ala | Alanine |
| Arg | Arginine |
| Asn | Asparagine |
| Asp | Aspartic acid |
| Cys | Cysteine |
| Glu | Glutamic acid |
| Gln | Glutamine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |
| Abbreviation* | Modified and Unusual Amino Acid |
| Aaa—$CO_2$R | An amino acid ester, for examples: Gly—$CO_2$Bn is Glycine, benzyl ester; Ser(OBn)—$CO_2$Me is O-Benzyl-serine, methyl ester. |
| (N—R)Aaa | (N—Me)His is N(α)-methyl-histidine; (N-(4-BnO—Bn)Gly is N-(4-phenylmethoxybenzyl)-glycine. |
| Aaa—CONHR | An amino acid amide, for examples: Gly—CONHBn is Glycine, N-benzyl amide; Ser(OBn)—CONHEt is O-Benzyl-serine, N-ethyl amide; Tyr(OBn)—CONHCH$_2$CH$_2$OBn is O-Benzyl-tyrosine, N-(2-(phenylmethoxy)-ethyl)amide; Cbz—His—CON(CH$_2$CH$_2$OBn)$_2$ is N(α)-phenylmethoxycarbonyl-histidine, N,N-bis-(2-phenylmethoxyethyl)amide. |
| Hcy | Homocysteine |
| Bal | Beta-alanine (or 3-aminopropionic acid) |
| His(1-Me) | 1-Methyl-histidine (or N(τ)-Methyl-histidine) |
| His(Tr) | 1-Triphenylmethyl-histidine (or N(τ)-Trityl-histidine) |
| Ser(OBn) | O-Benzyl-serine |
| Thr(OBn) | O-Benzyl-threonine |
| Tic | 1,2,3,4-Tetrahydro-3-isoquinoline-carboxylic acid |
| Tyr(OBn) | O-Benzyl-tyrosine |
| (α-Me)Tyr(OBn) | 2-Amino-3-(4-benzyloxyphenyl)-2-methyl-propionic acid (or α-Methyl-O-benzyl-tyrosine) |
| (N—Me)Tyr(OBn) | N-Methyl-O-benzyl-tyrosine |

TABLE OF ABBREVIATIONS

| Abbreviation | Protecting Group |
|---|---|
| Ac | Acetyl |
| Ada | 1-Adamantyl acetic acid |
| Adoc | Adamantyloxycarbonyl |
| Bn | Benzyl |
| MeBn | 4-Methylbenzyl |
| Cbz | Benzyloxycarbonyl |
| 2-Br—Cbz | ortho-Bromobenzyloxycarbonyl |
| 2-Cl—Cbz | ortho-Chlorobenzyloxycarbonyl |
| Bom | Benzyloxymethyl |
| Boc | tertiary Butyloxycarbonyl |
| Dnp | 2,4-Dinitrophenyl |
| For | Formyl |
| Fmoc | 9-Fluorenylmethyloxycarbonyl |
| NO$_2$ | Nitro |
| Tos | 4-Toluenesulfonyl (tosyl) |
| Tr | Triphenylmethyl (trityl) |
| Abbreviation | Solvents and Reagents |
| HOAc | Acetic acid |
| CF$_3$SO$_2$H | Trifluoromethanesulfonic acid |
| DCM | Dichloromethane |
| DCC | N,N'-Dicyclohexylcarbodiimide |
| DIC | N,N'-Diisopropylcarbodiimide |
| DIEA | N,N-Diisopropylethylamine |
| DMAP | 4-Dimethylaminopyridine |
| DMF | N,N'-Dimethylformamide |
| EDAC | N-Ethyl-N'-Dimethylaminopropyl-carbodiimide |
| EtOAc | Ethyl acetate |
| Et$_2$O | Diethyl ether |
| HCl | Hydrochloric acid |
| HF | Hydrofluoric acid |
| HOBT | 1-Hydroxybenzotriazole |
| KOH | Potassium hydroxide |
| MeCN | Acetonitrile |
| MeOH | Methanol |
| NMP | N-Methylpyrrolidone |
| NHOS | N-Hydroxysuccinimide |
| iPrOH | iso-Propanol |
| TFA | Trifluoroacetic acid |
| Abbreviation | Solid Phase Peptide Synthesis Resins |
| HMP Resin | 4-(Hydroxymethyl)-phenoxymethyl-polystyrene resin |
| MBHA Resin | Methylbenzhydrylamine resin |
| PAM Resin | 4-(Hydroxymethyl)-phenylacetamido-methyl-polystyrene resin |
| 2-Cl—Tr Resin | 2-Chlorotrityl-polystyrene resin |
| NH$_2$-Rink Resin | 4-(Amino-(2',4'-dimethoxyphenyl)-methyl)-phenoxymethyl-polystyrene resin |
| Wang Resin | 4-(Hydroxymethyl)phenoxymethyl-polystyrene resin |
| Abbreviation | Biological Reagents |
| FPP | Farnesyl pyrophosphate |
| PFT | Protein farnesyltransferase |
| DTT | Dithiothreitol |
| BSA | Bovine serum albumin |

*If the optical activity of the amino acid is other than L(S), the amino acid or abbreviation is preceded by the appropriate configuration D(R) or DL(RS).

Preferred compounds of the invention are of Formulas II and III,

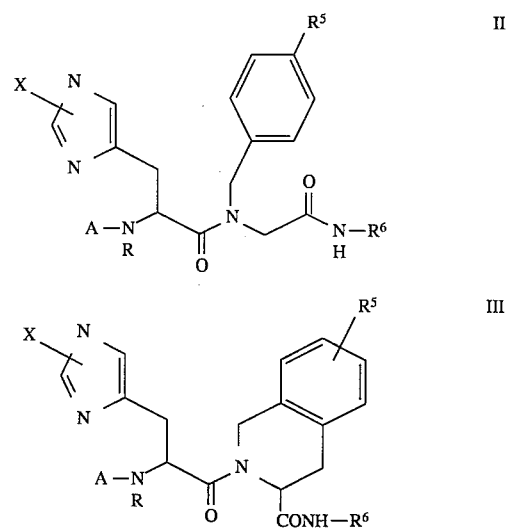

wherein:

A is limited to CO$_2$R$^2$, CONHR$^2$, C(S)OR$^2$, or C(S)NHR$^2$ with R$^2$ as defined below;

R=H or Me;

R$^2$ is limited to alkyl, (CH$_2$)$_m$-cycloalkyl, (CH$_2$)$_m$-aryl, (CH$_2$)$_m$-heteroaryl, with m=0, 1, 2, or 3;

R$^5$ is limited to (CH$_2$)$_m$-aryl, O-(CH$_2$)$_m$-aryl, or O-(CH$_2$)$_m$-heteroaryl with m as defined above;

R$^6$ is limited to (CH$_2$)$_n$-R$^5$, CH$_2$CO$_2$R$^2$, CH$_2$CONHR$^2$, with n=1 or 2, and with R$^5$ and R$^2$ as defined above; and X is limited to H or Me;

or a pharmaceutically acceptable salt thereof.

The most preferred compounds of the invention are of Formula II and III, wherein:

A is further limited to CO$_2$R$^2$ or CONHR$^2$, with R$^2$ as defined below;

R is limited to H;

R$^2$ is further limited to alkyl, or (CH$_2$)$_m$-aryl with m=0, 1, 2, or 3;

R$^5$ is further limited to (CH$_2$)$_m$-aryl or O-(CH$_2$)$_m$-aryl with m as defined above;

R$^6$ is limited to CH$_2$-R$^5$ or CH$_2$CONHR$^2$, with n=1 or 2, and with R$^5$ and R$^2$ as defined above; and X is limited to H or Me;

or a pharmaceutically acceptable salt thereof.

The present invention is also directed to the use of a compound of Formulas II and III, or a pharmaceutically acceptable salt thereof, to inhibit the activity of a protein farnesyltransferase enzyme as a method for treating tissue proliferative diseases.

A further embodiment of the present invention is the use of a pharmaceutical composition including a therapeutically effective amount of Formulas II and III, or a pharmaceutically acceptable salt thereof, as a method for the treatment of cancer.

A still further embodiment of the present invention is the use of a pharmaceutical composition including a therapeutically effective amount of Formulas II and III, or a pharmaceutically acceptable salt thereof, as a method for the treatment of restenosis.

A still further embodiment of the present invention is a pharmaceutical composition for administering a therapeutically effective amount of a compound of Formulas II and III, or a pharmaceutically acceptable salt thereof, in unit dosage form in the treatment methods mentioned above.

A final embodiment of the present invention pertains to methods for the preparation of compounds of Formulas II and III, or pharmaceutically acceptable salts thereof, by solid phase synthesis, solution phase synthesis, and simultaneous multiple syntheses using a Diversomer® apparatus.

GENERAL METHODS FOR THE PREPARATION, EVALUATION AND USE OF COMPOUNDS OF FORMULA I

The compounds of Formula I may be prepared according to the synthetic strategy described in Scheme I. The secondary amine derivatives may be prepared by a reductive amination of an appropriate aldehyde with an appropriate amine in the presence of a reducing agent such as sodium triacetoxyborohydride. The secondary amine may then be coupled in the presence of an activating agent such as DCC and HOBT to a histidine derivative suitably functionalized at the N-terminus.

Scheme I

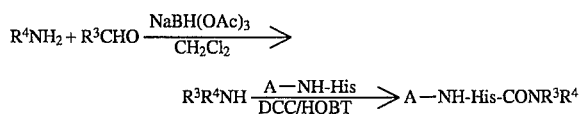

Additionally, compounds of Formula I may be prepared by simultaneous multiple solid phase syntheses using the Diversomer® apparatus described by DeWitt S. H., et al., proc. Natl. Acad. Sci. USA, 90:6909 (1993). For example (Scheme II below), Fmoc-His-OMe is linked to 2-Cl-Tr resin using a sterically hindered amine such as DIEA as an HCl scavenger, the Fmoc protecting group is removed with piperidine, the resulting free amino terminus is acylated with a series of isocyanates, activated esters, acid chlorides and the like, the ester is saponified, the resulting carboxylic acid is activated with a carbodiimide reagent such as EDAC, DCC, or DIC, the activated carboxyl group is reacted with alcohols such as HOBT, NHOS or pentachlorophenol to give an activated ester, the activated ester is reacted with a series of amines and the resulting array of compounds of Formula I is cleaved from the resin by with hot HOAc or by treatment with TFA in DCM at room temperature. An alternative Diversomer® method (Scheme III) uses N(1) or N(3)-carboxymethyl-Fmoc-His-OMe which is linked to either Wang resin or 2-Cl-Tr resin. The remainder of the synthesis parallels that described in Scheme II.

For all three synthetic methods described above, appropriate consideration is given to protection and deprotection of reactive functional groups and to the sequence of synthetic steps. Knowledge of the use of common protecting groups and strategy for the assembly of complex organic molecules are within the usual realm of expertise of a practitioner of the art of organic chemistry (see, for example, Greene T. W. and Wuts P. G. M., *Protective Groups in Organic Chemistry,* John Wiley and Sons (1991); Corey E. J. and Cheng X. -M., *The Logic of Chemical Synthesis,* John Wiley and Sons (1989)).

The homogeneity and composition of the resulting compounds is verified by HPLC, capillary electrophoresis, thin layer chromatography (TLC), proton nuclear magnetic resonance spectrometry (NMR), fast atom bombardment mass spectrometry (FAB-MS) and electrospray mass spectrometry (ES-MS).

SCHEME II:
Multiple Simultaneous Synthesis Method

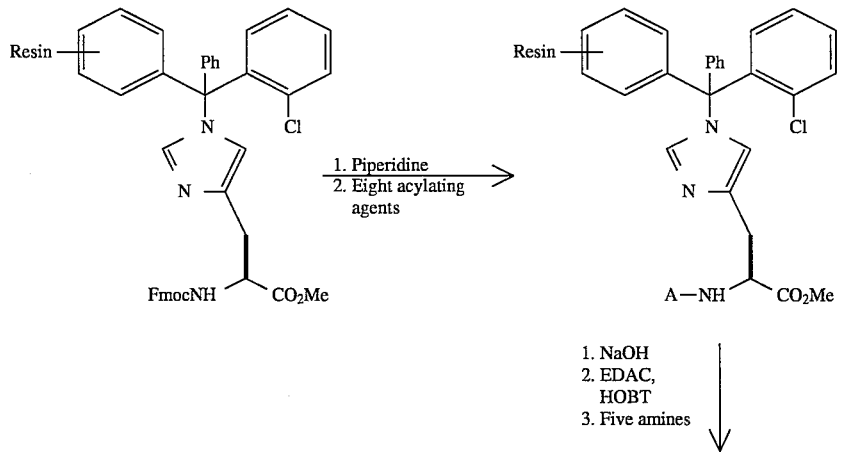

-continued
SCHEME II:
Multiple Simultaneous Synthesis Method

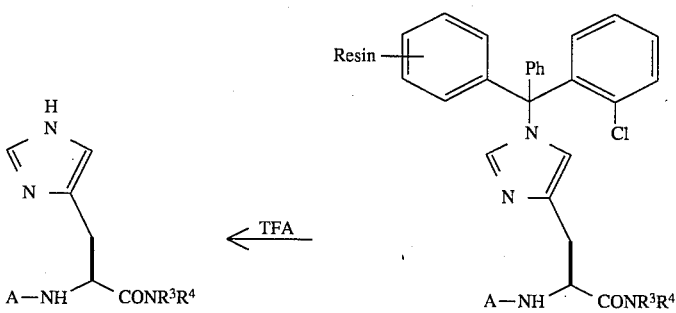

40 Compounds of Formula I

SCHEME III:
Alternate Multiple Simultaneous Method

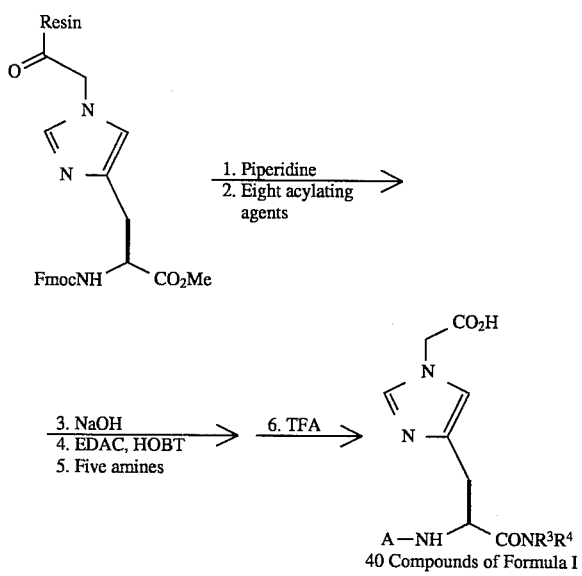

40 Compounds of Formula I

As discussed above, the compounds of Formulas I–III are capable of further forming both pharmaceutically acceptable acid addition and/or base salts. All of these forms are within the scope of the present invention.

Pharmaceutically acceptable acid addition salts of the compounds of Formulas I–III include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, Berge S. M., et al., "Pharmaceutical Salts," *Journal of Pharmaceutical Science*, 66:1–19 (1977)).

The acid addition salts of said basic compounds are prepared by contacting the free base form with a sufficient amount of the desired acid to produce the salt in the conventional manner. Preferably a compound of Formulas I–III can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts", *Journal of Pharmaceutical science*, 66:1–19 (1977)).

The base addition salts of said acidic compounds are prepared by contacting the free acid form with a sufficient amount of the desired base to produce the salt in the conventional manner. Preferably, a compound of Formulas I–III can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in the R(D) or S(L) configuration. The present invention includes all enantiomeric and epimeric forms as well as the appropriate mixtures thereof.

The PFT inhibitory activity of compounds of Formulas I–III was assayed in 30 mM potassium phosphate buffer, pH 7.4, containing 7 mM DTT, 1.2 mM $MgCl_2$, 0.1 mM leupeptin, 0.1 mM pepstatin, and 0.2 mM phenylmethylsulfonyl fluoride. Assays were performed in 96 well plates (Wallec) and employed solutions composed of varying concentrations of a compound of Formula I in 100% DMSO. Upon addition of both substrates, radiolabeled farnesyl pyrophosphate ($[1-^3H]$, specific activity 15–30 Ci/mmol, final concentration 0.12 µM) and (biotinyl)-Ahe-Tyr-Lys-Cys-Val-Ile-Met peptide (SEQ ID NO:1) (final concentration 0.1 µM), the enzyme reaction was started by addition of 40-fold purified rat brain farnesyl protein transferase. After incubation at 37° C. for 30 minutes, the reaction was terminated by diluting the reaction 2.5-fold with a stop buffer containing 1.5M magnesium acetate, 0.2M $H_3PO_4$, 0.5% BSA, and strepavidin beads (Amersham) at a concentration of 1.3 mg/mL. After allowing the plate to settle for 30 minutes at room temperature, radioactivity was quantitated on a microBeta counter (Model 1450, Wallec). Compounds of Formulas I–III show $IC_{50}$ values of 0.5 to 1000 nM in this assay and are thus valuable inhibitors of protein:farnesyltransferase enzyme which may be used in the medical treatment of tissue proliferative diseases, including cancer and restenosis.

The compounds of the present invention can be prepared and administered in a wide variety of oral, rectal and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formulas I–III or a corresponding pharmaceutically acceptable salt of a compound of Formulas I–III.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as inhibitors of PFT, the compounds utilized in the pharmaceutical methods of this invention are administered at the initial dosage of about 0.01 mg to about 20 mg per kilogram daily. A daily dose range of about 0.01 mg to about 10 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention.

EXAMPLE 1

N-[(Phenylmethoxy)carbonyl]-L-histidyl-N-[2-(phenylmethoxy)ethyl]-N$^2$-[[4-(phenylmethoxy)phenyl]methyl]-glyciniamide

Step 1: (4-Benzylorybenzylamino)acetic acid methyl ester

To a mixture of glycine methyl ester hydrochloride (2.07 g, 16.5 mmol) and 4-benzyloxybenzaldehyde (3.18 g, 15.0 mmol) in CH$_2$Cl$_2$ (50 mL) at 0° C. was added sodium triacetoxyborohydride (3.81 g, 18.0 mmol). The mixture was allowed to warm to room temperature and stirred for 4 hours. Aqueous NaHCO$_3$ was added and the mixture was stirred for 30 minutes. The aqueous layer was extracted three times with CH$_2$Cl$_2$. The combined organic extracts were washed with brine, dried over MgSO$_4$, and concentrated. Flash chromatography (75% EtOAc/hexane) gave 1.98 g (46%) of the title compound as a white solid, mp 57°–58° C.

Step 2: N-[N-[(Phenylmethoxy)carbonyl]-L-histidyl]-N-[[4-(phenylmethoxy)phenyl]methyl]glycine methyl ester To a suspension of CBZ-histidine (1.22 g, 4.21 mmol) in DMF (10 mL) was added HOBT hydrate (0.77 g, 5.05 mmol) and DCC (1.04 g, 5.05 mmol). The amine from Step 1 above (1.20 g, 4.21 mmol) was then added and the mixture was stirred at room temperature overnight. The mixture was filtered, and the filtrate was diluted with CHCl$_3$, washed twice with saturated NaHCO$_3$, brine, dried over MgSO$_4$, and concentrated. Flash chromatography gave 1.68 g (72%) of the title compound as a white foam; ES-MS 557 (m+1).

Step 3: N-[N-[(Phenylmethoxy)carbonyl]-L-histidyl]-N-[[4-(phenylmethoxy)phenyl]methyl]glycine To a solution of the ester from Step 2 (1.53 g, 2.75 mmol) in THF (15 mL) and H$_2$O (5 mL) at 0° C. was added LiOH hydrate (0.14 g, 3.30 mmol) and the solution was stirred 5 hours at 0° C. The solution was concentrated, the residue taken up in H$_2$O, and the pH was adjusted to 4–5 with 1N HCl. The resulting mixture was concentrated and dried in vacuo to afford 1.65 g of the title compound as a white solid; FAB-MS 543 (m+1). Anal. calcd. for C$_{30}$H$_{30}$N$_4$O$_6$·1.2 LiCl·2.0H$_2$O: C, 57.24; H, 5.44; N, 8.90. Found: C, 57.35; H, 5.32; N, 8.62.

Step 4: N-[(Phenylmethoxy)carbonyl]-L-histidyl-N-[2-(phenylmethoxy)ethyl]-N$^2$-[[4-(phenylmethoxy)phenyl]methyl]glycinamide To a solution of the acid from Step 3 (2.9 g, 5.33 mmol) in DMF (15 mL) was added HOBT hydrate (0.98 g, 6.39 mmol) and DCC (1.32 g, 6.39 mmol) followed by 2-benzyloxyethylamine hydrochloride (1.0 g, 5.33 mmol). Et$_3$N (0.82 mL, 5.86 mmol) was added and the mixture was stirred overnight at room temperature. The mixture was filtered and the filtrate was diluted with CHCl$_3$, washed twice with saturated NaHCO$_3$, brine, dried over MgSO$_4$, and concentrated. Flash chromatography (2–5% MeOH/CHCl$_3$) gave 2.25 g (63%) of the title compound as a white foam; ES-MS 676 (m+1).

EXAMPLE 2

N-[(Phenylmethoxy)carbonyl]-L-histidyl-N-[2-(1H-indol-3-yl)ethyl-N$^2$-[[4-(phenylmethoxy)phenyl]methyl]glycinamide According to Example 1, Step 4, by substituting tryptamine hydrochloride for 2-benzyloxyethylamine hydrochloride, the title compound was obtained as a white foam; ES-MS 685 (m+1).

EXAMPLE 3

N-[N-[N-[(Phenylmethoxy)carbonyl]-L-histidyl]-N-[[4-(phenylmethoxy)phenyl]methyl]glycyl]glycine phenylmethyl ester According to Example 1, Step 4, by substituting glycine benzyl ester hydrochloride for 2-benzyloxyethylamine hydrochloride, the title compound was obtained as a white powder; ES-MS 690 (m+1).

EXAMPLE 4

N-[(Phenylmethoxy)carbonyl]-L-histidyl-N-(4-phenylbutyl)-N$^2$-[[4-(phenylmethoxy)phenyl]methyl]glycinamide According to Example 1, Step 4, by substituting 4-phenybutylamine for 2-benzyloxyethylamine hydrochloride and omitting Et$_3$N, the title compound was obtained as a white foam, mp 58°–61° C.; ES-MS 674 (m+1).

EXAMPLE 5

N-[N-[N-[(Phenylmethoxy)carbonyl]-L-histidyl]-N-[[4-(phenylmethoxy)phenyl]methyl]glycyl]glycine methyl ester According to Example 1, Step 4, by substituting glycine methyl ester hydrochloride for 2-benzyloxyethylamine, the title compound was obtained as a white foam; ES-MS 614 (m+1).

EXAMPLE 6

N-[(Phenylmethoxy)carbonyl]-L-histidyl-N-[[4-(phenylmethoxy)phenyl]methyl]glycyl-N-phenylmethylglycinamide According to Example 1, Step 4, by substituting N-phenylmethylglycinamide trifluoroacetic acid salt for 2-benzyloxyethylamine hydrochloride, the title compound was obtained as a white powder; ES-MS 689 (m+1).

EXAMPLE 7

N-[N-[N-[(Phenylmethoxy)carbonyl]-L-histidyl]-N-[[4-(phenylmethoxy)phenyl]methyl]glycyl]-β-alanine phenylmethyl ester According to Example 1, Step 4, by substituting β-alanine benzyl ester hydrochloride for 2-benzyloxyethylamine hydrochloride, the title compound was obtained as a white foam; ES-MS 704 (m+1).

EXAMPLE 8

N-[N-[(4-Methoxyphenyl)methyl]-N-[N-[(phenylmethoxy)carbonyl]-L-histidyl]glycyl]glycine phenylmethyl ester Step 1: N-(4-Methoxybenzylamino)acetic acid ethyl ester To a mixture of glycine ethyl ester hydrochloride (1.03 g, 7.38 mmol) and 4-methoxybenzaldehyde (0.71 g, 5.21 mmol) in $CH_2Cl_2$ (25 mL) was added KOAc (0.51 g, 5.21 mmol) followed by sodium triacetoxyborohydride (1.44 g, 6.78 mmol). The mixture was stirred at room temperature for 4 hours. Aqueous $NaHCO_3$ was added and the mixture was stirred for 30 minutes. The aqueous layer was extracted three times with $CH_2Cl_2$. The combined organic extracts were washed with brine, dried over $MgSO_4$, and concentrated. Flash chromatography (60% EtOAc/hexane) gave 1.0 g (86%) of the title compound as a colorless oil; CI-MS 224 (m+1).

Step 2:
N-[(4-Methoxyphenyl)methyl]-N-[N-[(phenylmethoxy)carbonyl]-L-histidyl]glycine ethyl ester According to Example 1, Step 2, by substituting the compound from Step 1 above for N-[[4-(phenylmethoxy)phenyl]methyl]glycine methyl ester, the title compound was obtained as a white foam; ES-MS 495 (m+1).

Step 3:
N-[(4-Methoxyphenyl)methyl]-N-[N-[(phenylmethoxy)carbonyl]-L-histidyl]glycine According to Example 1, Step 3, but substituting the compound from Step 2 above for N-[N-[(phenylmethoxy)carbonyl]-L-histidyl]-N-[[4-(phenylmethoxy)phenyl]methyl]glycine methyl ester, the title compound was obtained as a white solid.

Step 4:
N-[(4-Methoxyphenyl)methyl]-N-[N-[(phenylmethoxy)carbonyl]-L-histidyl]glycine phenylmethyl ester To a solution of the acid from Step 3 (0.41 g, 0.88 mmol) in DMF (5 mL) was added HOBT hydrate (0.16 g, 1.05 mmol) and DCC (0.22 g, 1.05 mmol) followed by glycine benzyl ester hydrochloride (0.18 g, 0.88 mmol). $Et_3N$ (0.12 mL, 0.88 mmol) was added and the mixture was stirred overnight at room temperature. The mixture was filtered, the filtrate was diluted with $CHCl_3$, washed twice with saturated $NaHCO_3$, brine, dried over $MgSO_4$, and concentrated. Flash chromatography (2–5% MeOH/$CHCl_3$) gave 0.29 g (54%) of the title compound as a white foam; ES-MS 614 (m+1).

EXAMPLE 9

N-[(4-Methoxyphenyl)methyl]-N-[N-[(phenylmethoxy)carbonyl]-L-histidyl]glycine phenylmethyl ester According to Example 8, Step 4, by substituting benzyl alcohol for glycine benzyl ester hydrochloride and omitting $Et_3N$, the title compound was obtained as a white foam; ES-MS 557 (m+1).

EXAMPLE 10

N-[(Phenylmethoxy)carbonyl]-D-histidyl-N-[2-(phenylmethoxy)ethyl]-$N^2$-[[4-(phenylmethoxy)phenyl]methyl]glycinamide

Step 1:
N-BOC-N-[2-(phenylmethoxy)ethyl]glycinamide

To a solution of BOC-glycine (0.47 g, 2.69 mmol) in EtOAc (10 mL) was added HOBT hydrate (0.49 g, 3.22 mmol) followed by DCC (0.66 g, 3.22 mmol). After 30 minutes, a solution of benzyloxyethylamine (0.41 g, 2.69 mmol) in EtOAc (5 mL) was added and the mixture was stirred overnight at room temperature. The mixture was filtered, and the filtrate was diluted with EtOAc, washed with saturated aqueous $NaHCO_3$, brine, dried over $MgSO_4$, and concentrated. Flash chromatography (EtOAc) gave 0.72 g (87%) of the title compound as a light yellow oil which slowly solidified; CI-MS 309 (m+1).

Anal. calcd. for $C_{16}H_{24}N_2O_4$: C, 62.32; H, 7.84, N, 9.08. Found: C, 61.94; H, 7.83; N, 9.12.

Step 2: N-[2-phenylmethoxy)ethyl]glycinamide trifluoroacetic acid salt

To a solution of the compound from Step 1 above (0.67 g, 2.17 mmol) in $CH_2Cl_2$ (10 mL) was added TFA (1 mL). The solution was stirred at room temperature for 4 hours and then concentrated. The residue was twice taken up in $CH_2Cl_2$ and reconcentrated. Obtained 0.78 g of a light yellow gum which was used in Step 3 without further purification; CI-MS 209 (m+1).

Step 3:
N-[2-(Phenylmethoxy)ethyl]-$N^2$-[[4-(phenylmethoxy)phenyl]methyl]glycinamide To a solution of the compound from Step 2 above (0.69 g, 2.14 mmol) in $CH_2Cl_2$ (10 mL) at 0° C. was added 4-benzyloxybenzaldehyde (0.45 g, 2.14 mmol) followed by sodium triacetoxyborohydride (0.59 g, 2.78 mmol). The mixture was allowed to warm to room temperature and stirred for six hours. Saturated aqueous $NaHCO_3$ was added and the mixture was stirred for 30 minutes. The aqueous layer was extracted three times with $CH_2Cl_2$. The combined organic extracts were washed with brine, dried over $MgSO_4$, and concentrated. Flash chromatography (2–5% MeOH/$CHCl_3$) gave 0.46 g (53%) of the title compound as a colorless oil; CI-MS 405 (m+1).

Step 4:
N-[(Phenylmethoxy)carbonyl]-D-histidyl-N-[2-(phenylmethoxy)ethyl]-$N^2$-[[4-(phenylmethoxy)phenyl]methyl]glycinamide To a suspension of CBZ-D-histidine (0.093 g, 0.32 mmol) in DMF (2 mL) was added HOBT hydrate (0.059 g, 0.39 mmol) followed by DCC (0.080 g, 0.39 mmol). A solution of the compound from Step 3 above (0.13 g, 0.32 mmol) in DMF (2 mL) was added and the mixture was stirred overnight at room temperature. The mixture was filtered, and the filtrate was diluted with $CHCl_3$, washed twice with saturated aqueous $NaHCO_3$, brine, dried over $MgSO_4$, and concentrated. Flash chromatography (2–5% MeOH/$CHCl_3$) gave 0.10 g (45%) of the title compound as a white powder; ES-MS 676 (m+1).

Anal. calcd. for $C_{39}H_{41}N_5O_6 \cdot 0.5H_2O$: C, 68.39; H, 6.18; N, 10.22. Found: C, 68.56; H, 6.28; N, 9.83.

EXAMPLE 11

N-[(Phenylmethoxy)carbonyl]-L-histidyl-$N^2$-[(1,1'-biphenyl)-4-ylmethyl]-N-[2-(phenylmethyl)ethyl]glycinamide

Step 1:
$N^2$-[(1,1'-Biphenyl)-4-ylmethyl]-N-[2-phenylmethoxy)ethyl]glycinamide According to Example 10, Step 3, by substituting 4-biphenylcarboxaldehyde for 4-benzyloxybenzaldehyde, the title compound was obtained as a colorless oil which slowly solidified;

$^1$H NMR (300 MHz, CDCl$_3$): δ 7.65–7.27 (m, 15H), 4.55 (s, 2H), 3.82 (s, 2H), 3.62–3.50 (m, 4H), 3.35 (s, 2H).

Step 2:
N-[(Phenylmethoxy)carbonyl]-L-histidyl-$N^2$-[(1,1'-biphenyl)-4-ylmethyl]-N-[2-pheynylmethoxy)ethyl]glycinamide According to Example 10, Step 4, by substituting the compound from Step 1 above for N-[2-(phenylmethoxy)ethyl]-$N^2$-[[4-(phenylmethoxy)phenyl]methyl]glycinamide and CBZ-histidine for CBZ-D-histidine, the title compound was obtained as a white foam; ES-MS 646 (m+1).

EXAMPLE 12

N-[(Phenylmethoxy)carbonyl]-L-histidyl-$N^2$-[4-(phenylmethoxy)butyl]-N-[2-(phenylmethoxy)ethyl]glycinamide

Step 1: $N^2$-[4-(Phenylmethoxy)butyl]-N-[2-(phenylmethoxy)ethyl]glycinamide According to Example 10, Step 3, by substituting 4-benzyloxybutyraldehyde for 4-benzyloxybenzaldehyde, the title compound was obtained as a colorless oil;

$^1$H NMR (300 MHz, CDCl$_3$): δ 7.58 (br m, 1H), 7.38–7.25 (m, 10H), 4.53 (s, 2H), 4.50 (s, 2H), 3.60–3.42 (m, 6H), 3.25 (s, 2H), 2.61 (m, 2H), 1.71–1.50 (m, 5H).

Step 2:
N-[(Phenylmethoxy)carbonyl]-L-histidyl-$N^2$-[4-(phenylmethoxy)butyl]-N-[2-(phenylmethoxy)ethyl]glycinamide According to Example 10, Step 4, by substituting the compound from Step 1 above for N-[2-(phenylmethoxy)ethyl]-$N^2$-[[4-(phenylmethoxy)phenyl]methyl]glycinamide and CBZ-histidine for CBZ-D-histidine, the title compound was obtained as a white foam; ES-MS 642 (m+1).

EXAMPLE 13

N-[(Phenylmethoxy)carbonyl]-L-histidyl-N-(3-phenoxypropyl)-$N^2$-[[4-(phenylmethoxy)phenyl]methyl]glycinamide

Step 1: N-(3-Phenoxypropyl)-$N^2$-[[4-(phenylmethoxy)phenyl]methyl]glycinamide According to Example 10, Step 3, by substituting N-(3-phenoxypropyl)glycinamide hydrochloride for N-[2-(phenylmethoxy)ethyl]glycinamide trifluoroacetic acid salt, the title compound was obtained as a colorless oil which slowly solidified, mp 55°–56° C.; CI-MS 405 (m+1).

Step 2:
N-[(Phenylmethoxy)carbonyl]-L-histidyl-N-(3-phenoxypropyl)-$N^2$-[[4-(phenylmethoxy)phenyl]methyl]glycinamide According to Example 10, Step 4, by substituting the compound from Step 1 above for N-[2-(phenylmethoxy)ethyl]-$N^2$-[[4-(phenylmethoxy)phenyl]methyl]glycinamide and CBZ-histidine for CBZ-D-histidine, the title compound was obtained as a white foam; ES-MS 676 (m+1).

EXAMPLE 14

N-[N-[N-[(Phenylmethoxy)carbonyl]-L-histidyl]-N-[[3-(phenylmethoxy)phenyl]methyl]glycyl]glycine-phenylmethyl ester

Step 1: N-BOC-glycylglycine benzyl ester

According to Example 10, Step 1, by substituting glycine benzyl ester hydrochoride for benzyloxyethylamine and adding 1 eq. of Et$_3$N, the title compound was obtained as a colorless oil; CI-MS 323 (m+1).

Step 2: Glycylglycine benzyl ester trifluoroacetic acid salt

According to Example 10, Step 2, by substituting the compound from Step 1 above for N-BOC-N-[2-(phenylmethoxy)ethyl]glycinamide, the title compound was obtained as a white solid; CI-MS 223 (m+1).

Anal. calcd. for $C_{11}H_{14}N_2O_3 \cdot CF_3CO_2H$: C, 46.43; H, 4.61; N, 8.33. Found: C, 46.43; H, 4.50; N, 8.33.

Step 3: N-[2-(Phenylmethoxy)ethyl]-N-[[3-(phenylmethoxy)phenyl]methyl]glycine benzyl ester According to Example 10, Step 3, by substituting 3-benzyloxybenzaldehyde for 4-benzyloxybenzaldehyde and the compound from Step 2 above for N-[2-phenylmethoxy)ethyl]glycinamide trifluoroacetic acid salt, the title compound was obtained as a colorless oil;

$^1$H NMR (300 MHz, CDCl$_3$): δ 7.74 (br m, 1H), 7.48–7.21 (m, 11H), 6.98 (s, 1H), 6.91 (m, 2H), 5.20 (s, 2H), 5.09 (s, 2H), 4.13 (d, J=6 Hz, 2H), 3.78 (s, 2H), 3.36 (s, 2H).

Step 4:
N-[N-[N-[(Phenylmethoxy)carbonyl]-L-histidyl]-N-[[3-(phenylmethoxy)phenyl]methyl]glycyl]glycine-phenylmethyl ester According to Example 10, Step 4, by substituting the compound from Step 3 above for N-[2-(phenylmethoxy)ethyl]-$N^2$-[[4-(phenylmethoxy)phenyl]methyl]glycinamide and CBZ-histidine for CBZ-D-histidine, the title compound was obtained as a white foam; ES-MS 690 (m+1).

EXAMPLE 15

(S)-[1-(1H-Imidazol-3-ylmethyl)-2-oxo-2-[[2-(phenylmethoxy)ethyl][4-(phenylmethoxy)phenyl]methyl]amino]ethyl]carbamic acid, phenylmethyl ester

Step 1: [[2-(phenylmethoxy)ethyl][4-(phenylmethoxy)phenyl]methyl]amine

To a solution of benzyloxyethylamine (0.75 g, 4.96 mmol) in CH$_2$Cl$_2$ (20 mL) at 0° C. was added 4-benzyloxybenzaldehyde (0.96 g, 4.51 mmol). Sodium triacetoxyborohydride (1.24 g, 5.86 mmol) was added followed by AcOH (0.26 mL, 4.51 mmol). The mixture was allowed to warm to room temperature and stirred for 4 hours. Saturated aqueous NaHCO$_3$ was added and the mixture was stirred for 30 minutes. The aqueous layer was extracted three times with CH$_2$Cl$_2$. The combined organic extracts were washed with brine, dried over MgSO$_4$, and concentrated. Flash chromatography (2% MeOH/CHCl$_3$) gave 1.04 g (66%) of the title compound as a colorless oil; CI-MS 348 (m+1).

Step 2:
(S)-[1-(1H-Imidazol-3-ylmethyl)-2-oxo-2-[[2-(phenylmethoxy)ethyl][4-(phenylmethoxy)phenyl]methyl]amino]ethyl]carbamic acid, phenylmethyl ester According to Example 10, Step 4, by substituting the compound from Step 1 above for N-[2-(phenylmethoxy)ethyl]-N$^2$-[[4-(phenylmethoxy)phenyl]methyl]glycinamide and CBZ-histidine for CBZ-D-histidine, the title compound was obtained as a white foam; ES-MS 619 (m+1).

Anal. calcd. for C$_{37}$H$_{38}$N$_4$O$_5$: C, 71.83; H, 6.19; N, 9.05. Found: C, 71.44; H, 6.19; N, 8.99.

EXAMPLE 16

(S)-[1-(1H-imidazol-3-ylmethyl)-2-oxo-2-[bis[[4-(phenylmethoxy)phenyl]methyl]amino]ethyl]carbamic acid, phenylmethyl ester Step 1:
Bis[[4-(phenylmethoxy)phenyl]methyl]amine According to Example 8, Step 1, by substituting 4-benzyloxybenzylamine hydrochloride for glycine ethyl ester hydrochloride and 4-benzyloxybenzaldehyde for 4-methoxybenzaldehyde, the title compound was obtained as a white solid; CI-MS 410 (m+1).

Step 2:
(S)-[1-(1H-imidazol-3-ylmethyl)-2-oxo-2-[bis[[4-(phenylmethoxy)phenyl]methyl]amino]ethyl]carbamic acid, phenylmethyl ester According to Example 10, Step 4, by substituting the compound from Step 1 above for N-[2-(phenylmethoxy)ethyl]-N$^2$-[[4-(phenylmethoxy)phenyl]methyl]glycinamide and CBZ-histidine for CBZ-D-histidine, the title compound was obtained as a white foam; ES-MS 681 (m+1).

Anal. calcd. for C$_{42}$H$_{40}$N$_4$O$_5$: C, 74.10; H, 5.92; N, 8.23. Found: C, 73.87; H, 6.00; N, 8.15.

EXAMPLE 17

O-(Phenylmethyl)-N-[1,2,3,4-tetrahydro-2-[N-[(phenylmethoxy)carbonyl]-L-histidyl]-7-(phenylmethoxy)-L-3-isoquinolinecarbonyl]-L-serine methyl ester Step 1:
N-[N-BOC-[1,2,3,4-tetrahydro-7-(phenylmethoxy)-L-3-isoquinolinecarbonyl]]-L-serine methyl ester To a solution of N-BOC-7-(phenylmethoxy)-L-3-isoquinoline carboxylic acid (0.50 g, 1.30 mmol) in EtOAc (10 mL) was added HOBT (0.24 g, 1.56 mmol) followed by DCC (0.32 g, 1.56 mmol). Serine methyl ester hydrochloride (0.32 g, 1.30 mmol) was added followed by Et$_3$N (0.22 mL, 1.56 mmol) and the mixture was stirred overnight at room temperature. The mixture was filtered, and the filtrate was diluted with EtOAc, washed with saturated aqueous NaHCO$_3$, brine, dried over MgSO$_4$, and concentrated. Flash chromatography (40% EtOAc/hexane) gave 0.67 g (89%) of the title compound as a sticky foam; CI-MS 575 (m+1).

Anal. calcd. for C$_{33}$H$_{38}$N$_2$O$_7$: C, 68.97; H, 6.67; N, 4.87. Found: C, 68.57; H, 6.79; N, 4.99.

Step 2:
N-[1,2,3,4-tetrahydro-7-(phenylmethoxy)-L-3-isoquinolinecarbonyl]-L-serine methyl ester trifluoroacetic acid salt According to Example 10, Step 2, by substituting the compound from Step 1 above for N-BOC-N-[2-(phenylmethoxy)ethyl]glycinamide, the title compound was obtained as a white solid; CI-MS 475 (m+1).

Step 3:
O-(Phenylmethyl)-N-[1,2,3,4-tetrahydro-2-[N-[(phenylmethoxy)carbonyl]-L-histidyl]-7-(phenylmethoxy)-L-3-isoquinolinecarbonyl]-L-serine methyl ester According to Example 10, Step 4, by substituting the compound from Step 2 above for N-[2-(phenylmethoxy)ethyl]-N$^2$-[[4-(phenylmethoxy)phenyl]methyl]glycinamide and CBZ-histidine for CBZ-D-histidine, the title compound was obtained as a white solid, mp 82°–88° C.; ES-MS 746 (m+1).

EXAMPLE 18

[1-(1H-imidazol-4-ylmethyl)-2-oxo-2-[1,2,3,4-tetrahydro-7-(phenylmethoxy)-3-[[2-(phenylmethoxy)ethyl]amino]carbonyl]-2-isoquinolinyl]ethyl]carbamic acid, phenylmethyl ester Step 1:
N-[BOC-1,2,3,4-tetrahydro-7-(phenylmethoxy)-L-3-isoquinolinyl]-N'-[2-(phenylmethoxy)ethyl]carboxamide According to Example 17, Step 1, by substituting benzyloxyethylamine for serine methyl ester hydrochloride and omitting Et$_3$N, the title compound was obtained as a colorless oil; CI-MS 517 (m+1).

Step 2:
N-[1,2,3,4-tetrahydro-7-(phenylmethoxy)-L-3-isoquinolinyl]-N'-[2-(phenylmethoxy)ethyl]carboxamide According to Example 17, Step 2, by substituting the compound from Step 1 above for N-[1,2,3,4-tetrahydro-7-(phenylmethoxy)-L-3-isoquinolinecarbonyl]-L-serine methyl ester trifluoroacetic acid salt, the title compound was obtained as a light yellow oil; CI-MS 417 (m+1).

Step 3:
[1-(1H-imidazol-4-ylmethyl)-2-oxo-2-[1,2,3,4-tetrahydro-7-(phenylmethoxy)-3-[[2-(phenylmethoxy)ethyl]amino]carbonyl]-2-isoquinolinyl]ethyl]carbamic acid, phenylmethyl ester According to Example 10, Step 4, by substituting the compound from Step 2 above for N-[2-(phenylmethoxy)ethyl]-N$^2$-[[4-(phenylmethoxy)phenyl]methyl]glycinamide, the title compound was obtained as a mixture of separable diastereomers; Diastereomer A: ES-MS 688 (m+1); Diastereomer B: ES-MS 688 (m+1).

EXAMPLE 19

1-(2-Methoxy-2-oxoethyl)-N-[(phenyl-methoxy)carbonyl]-L-histidyl-N-[2-(phenyl-methoxy)ethyl]-$N^2$-[[4-phenyl-methoxy)phenyl]methyl]glucinamide To a solution of N-[(phenylmethoxy)carbonyl]-L-histidyl-N-[2-(phenylmethoxy)ethyl]-N'-[[4-(phenylmethoxy)phenyl]methyl]glycinamide (Example 1) (1.00 g, 1.48 mmol) in $CH_2Cl_2$ (10 mL) was added $(iPr)_2NEt$ (0.28 mL, 1.63 mmol) followed by methyl bromoacetate (0.14 mL, 1.48 mmol). The solution was stirred for two days at room temperature. After concentration and flash chromatography (1–2% $MeOH/CHCl_3$), 0.91 g (82%) of the title compound was obtained as a white foam; ES-MS 748 (m+1).

Anal. calcd. for $C_{42}H_{45}N_5O_8$: C, 67.46; H, 6.07; N, 9.36. Found: C, 67.09; H, 5.91; N, 9.12.

EXAMPLE 20

1-(Carboxymethyl)-N-[(phenylmethoxy)carbonyl]-L-histidyl-$N^2$-[[4-(phenoxymethyl)phenyl]methyl]-N-[2-(phenylmethoxy)ethyl]glycinamide According to Example 1, Step 3, by substituting the compound from Example 19 for N-[N-[(phenylmethoxy)carbonyl]-L-histidyl]-N-[[4-(phenylmethoxy)phenyl]methyl]glycine methyl ester, the title compound was obtained as a white powder; ES-MS 734 (m+1), 740 (m+Li).

EXAMPLE 21

Solid phase supported
N-[N-(9H-Fluoren-9-ylmethoxy)carbonyl-histidyl] methyl ester
{Fmoc-D-His-(2-Cl-Tr-Resin)-$CO_2$Me}

To a suspension of Fmoc-His-$CO_2$Me (1.0 mmol) in $CCl_3$H (10 mL) was added 2-chlorotrityl chloride resin (Novabiochem) (1.0 g) followed by DIEA (1.1 mmol). The resulting mixture was subjected to brief sonication to disperse the resin and then agitated on a shaker for 2.5 hours. The modified resin was collected by filtration, washed with $CHCl_3$ (5×10 mL) and dried in vacuo for 18 hours to yield the loaded resin.

EXAMPLE 22

Methyl
{(4-Benzyloxy-benzyl)-[2-(3-benzyl-ureido)-3-(3H-imidazol-4-yl)propionyl]amino}acetic acid ester Fmoc-His(2-Cl-Tr-resin)-$CO_2$Me (from Example 21 above, 0.15 mmol) was suspended in 20% piperidine in DMF (v/v, 4 mL). The resulting suspension was subjected to sonication for 10 minutes and then agitated by shaking for 30 minutes. The resin was filtered and washed with DMF three times. The resin was again subjected to the same reaction conditions for an additional 20 minutes. The resin was filtered and washed with DMF four times, $CHCl_3$ three times to provide His(2-Cl-Tr-resin)-$CO_2$Me which was suspended in DCM (10 mL), agitated for 10 minutes by shaking, treated with benzyl isocyanate (0.6 mmol) and agitated an additional 30 minutes. The resin was filtered, washed with DCM three times, resuspended in DCM and the benzyl isocyanate treatment was repeated. The resin was filtered and washed with DMF two times, and $CHCl_3$ five times to give BnNHCO-His(2-Cl-Tr-resin)-$CO_2$Me which was next suspended in a 3:1 mixture of dioxane/MeOH (3 mL) and treated with aqueous 1.0N NaOH (0.6 mmol). The suspension was agitated by shaking for 18 hours, filtered, washed sequentially with a 2:1 mixture of dioxane and 10% aqueous citric acid (3×10 mL), dioxane/MeOH (3×10 mL) and $CHCl_3$ (3×10 mL) to provide BnNHCO-His(2-Cl-Tr-resin)-$CO_2$H. The BnNHCO-His(2-Cl-Tr-resin)-$CO_2$H was suspended in DMF (4 mL) and treated with a carbodiimide coupling reagent such as DIC (0.6 mmol) and HOBT (0.6 mmol). The resulting mixture was stirred 30 minutes and (4-benzyloxybenzylamino)acetic acid methyl ester (0.6 mmol) was added. The resulting mixture was shaken 18 hours before filtering the resin and washing with DMF three times and $CHCl_3$ three times. The resin was suspended in DMF (10 mL) and the carbodiimide/BT/4-benzyloxybenzylamino acetic acid methyl ester coupling reaction was repeated. After 18 hours the resin was filtered and washed with 10 mL each of MeOH two times, DCM three times, DMF two times, MeOH two times, and $CHCl_3$ two times to give BnNHCO-His(2-Cl-Tr-resin)-$CON(CH_2CO_2Me)CH_2$-(4-BnO-Ph). The substituted dipeptide was cleaved from the resin by treatment with 70% TFA in DCM, shaking for 1 hour at room temperature. The supernate containing the free dipeptide was filtered away from the resin and the resin washed with DCM three times. The combined supernate and washings were concentrated in vacuo to provide BriNHCO-His-$CON(CH_2CO_2Me)CH_2$-(4-BnO-Ph).TFA. The product was partitioned between water and DCM and both layers were treated dropwise with saturated aqueous $NaHCO_3$ until the aqueous layer remained basic. The layers were separated and the organic phase was washed with saturated aqueous NaCl and dried ($MgSO_4$). Filtration and concentration yielded BnNHCO-His-$CON(CH_2CO_2Me)CH_2$-(4-BnO-Ph).

EXAMPLE 23

Multiple, Simultaneous Solid Phase Synthesis

The method described in Example 22 may be employed in simultaneous multiple syntheses using the apparatus described by DeWitt S. H., et al., *Proc. Natl. Acad. Sci. USA*, 90:6909 (1993). Fmoc-His(2-Cl-tr-resin)$CO_2$Me prepared according to Example 21 (100–200 mg) is placed in each of 40 gas dispersion tubes and the tubes are placed in the multiple synthesis apparatus. The sequential deprotection and coupling reactions described in Example 22 are followed, employing the following acylating agents and amines in all possible combinations:

Acylating agents
1) benzyl isocyanate
2) benzyloxycarbonyl NHOS ester
3) phenyl isocyanate
4) 3-pyridylmethyl isocyanate
5) phenethyl isocyanate
6) butyl isocyanate
7) phenylacetyl chloride
8) 1-naphthyl isocyanate Amines
1) $HN(CH_2CO_2Me)CH_2$(4-BnO-Ph)
2) $HN(CH_2CONHCH_2CH_2OBn)CH_2$(4-BnO-Ph)
3) $HN(CH_2CONHCH_2CH_2SBn)CH_2$(4-BnO-Ph)

4) HN(CH₂CONHCH₂CH₂OBn)CH₂(4-EtO-Ph)
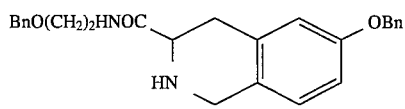
Following cleavage from the resin and work-up as described in Example 22, the following 40 substituted analogs of Formula I are isolated:
1. 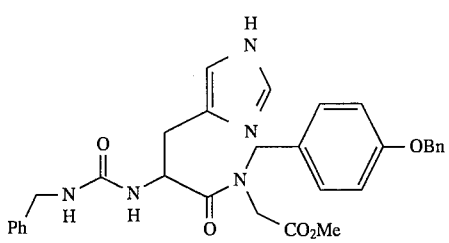
2. 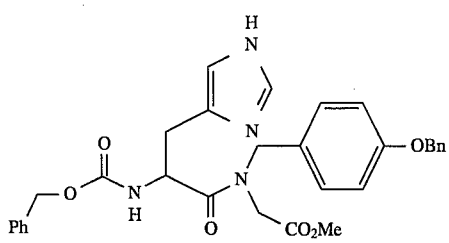
3. 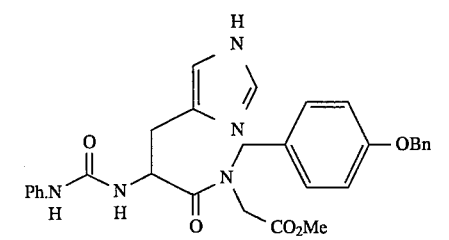
4. 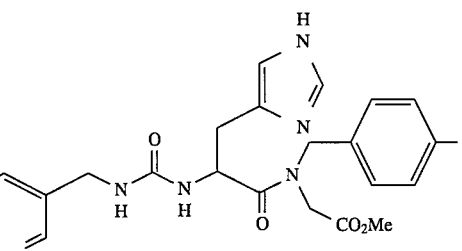
5. 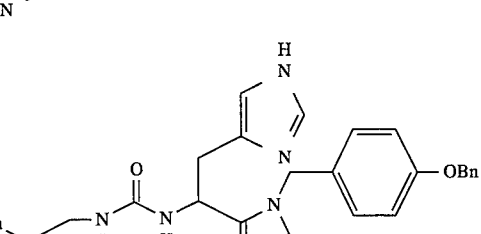
6. 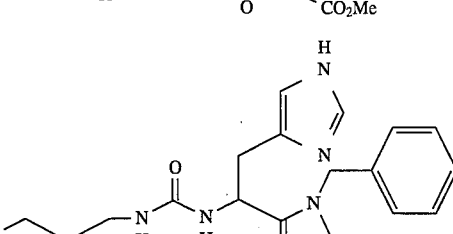
7. 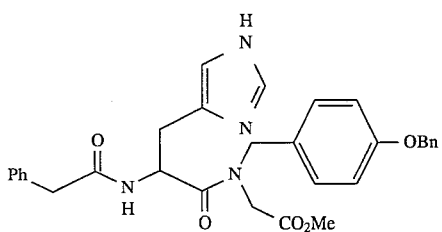
8. 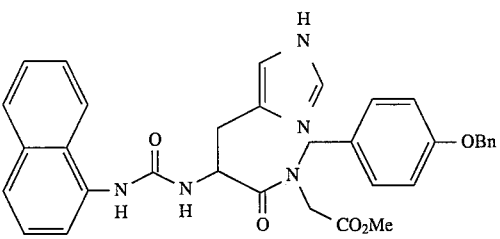
9. 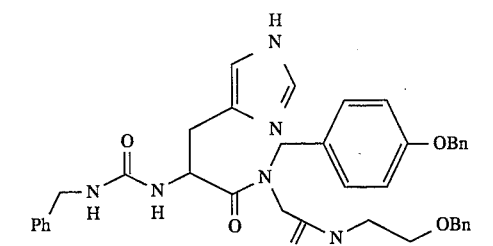
10. 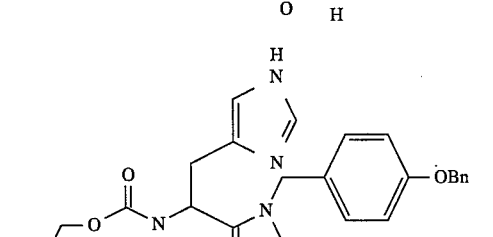
11. 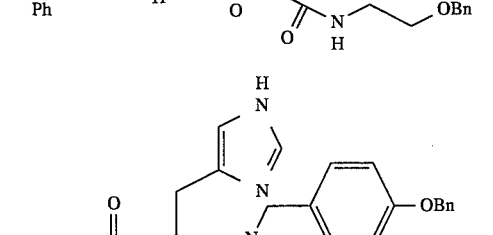
12. 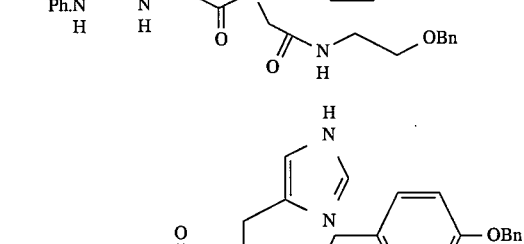

25
-continued
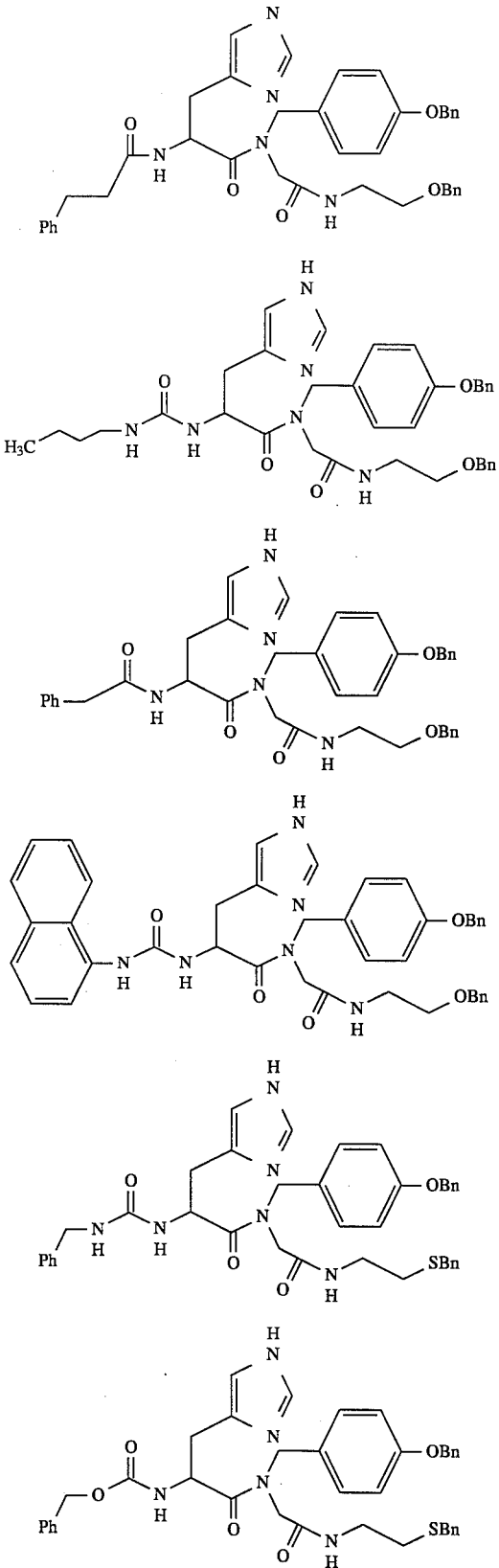
13.
14.
15.
16.
17.
18.
26
-continued
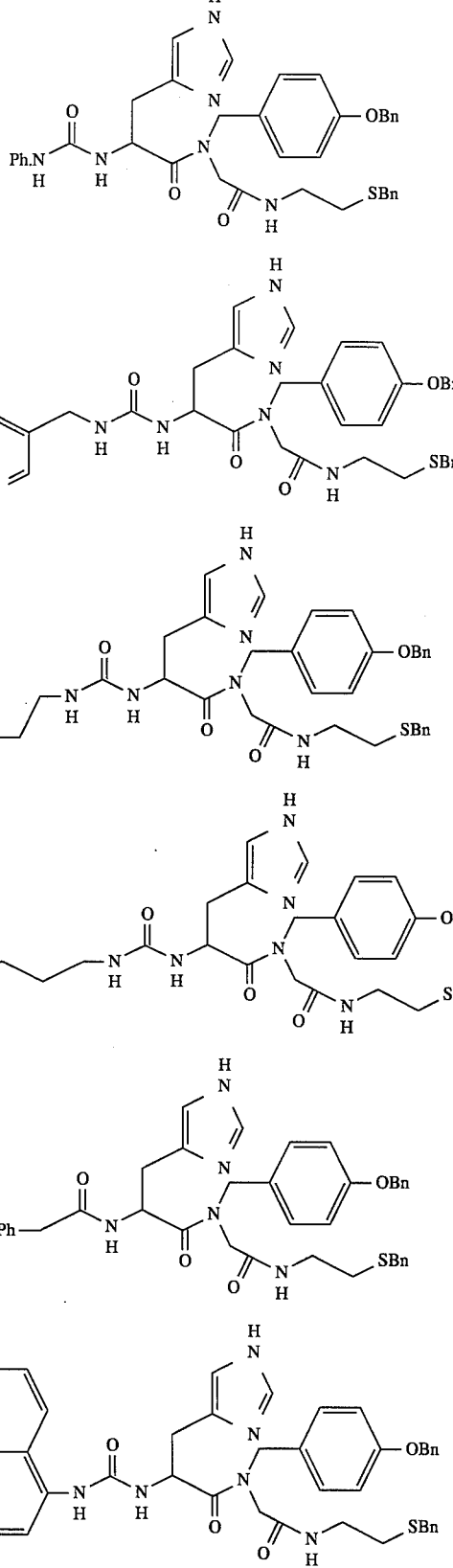
19.
20.
21.
22.
23.
24.

27
-continued
25. 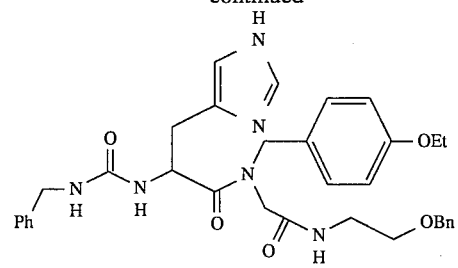
26. 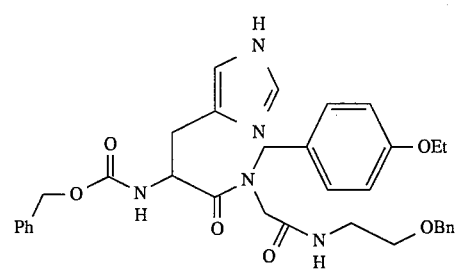
27. 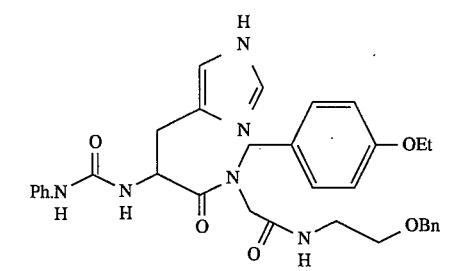
28. 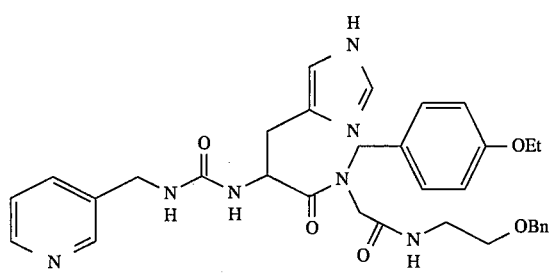
29. 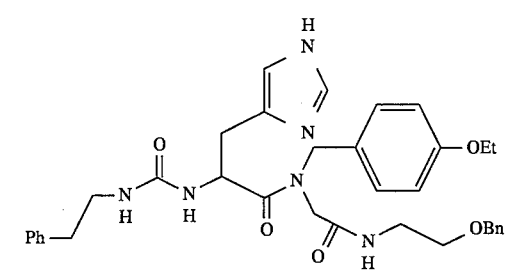
30. 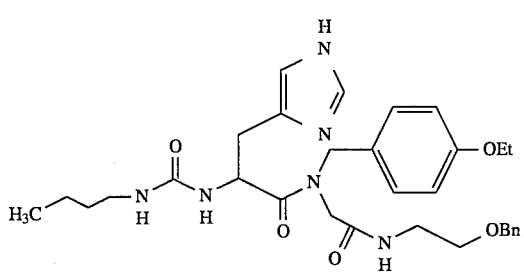
28
-continued
31. 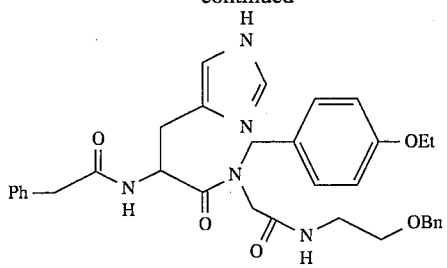
32. 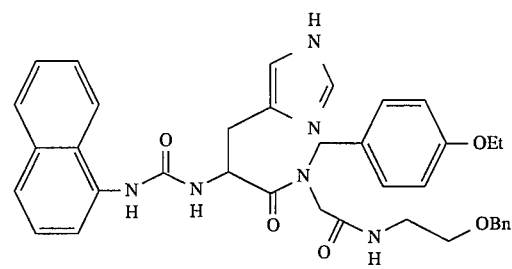
33. 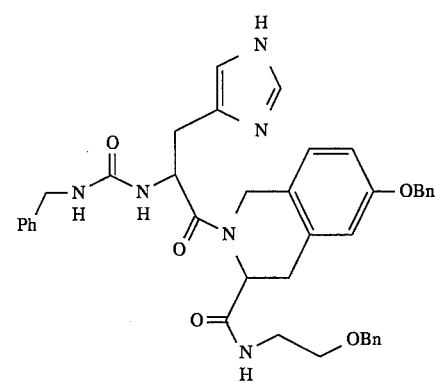
34. 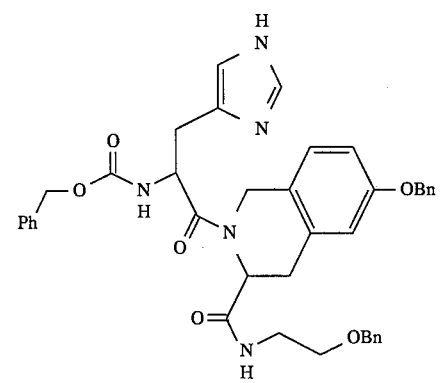
35. 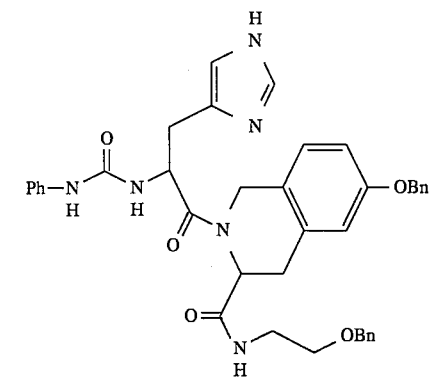

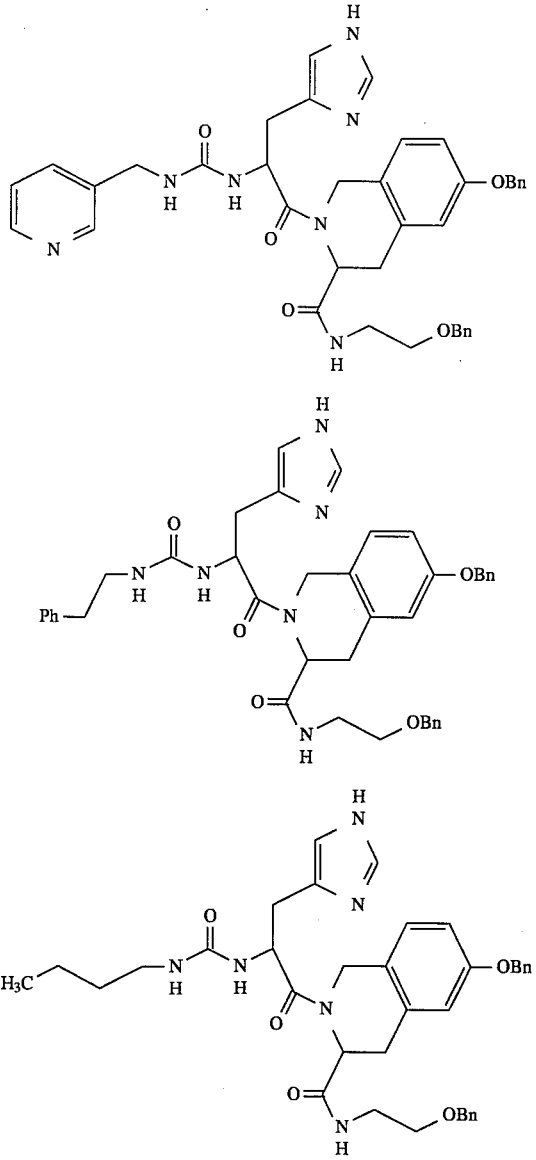

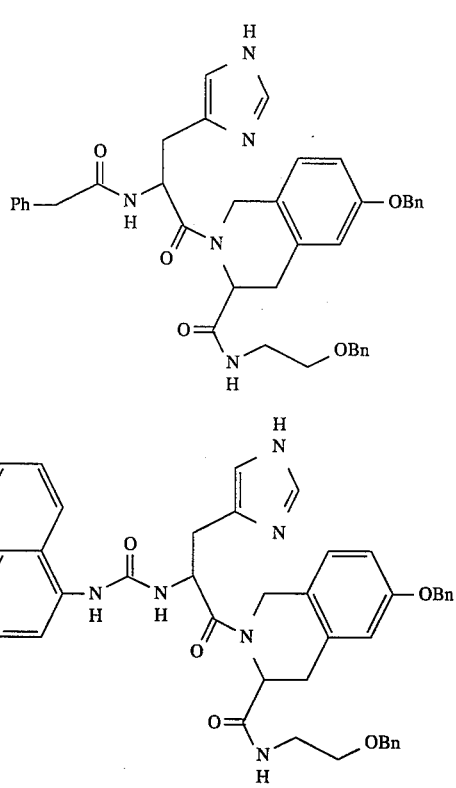

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:
1. An inhibitor of protein farnesyltransferase which is a histidine or homohistidine derivative of the Formula I,

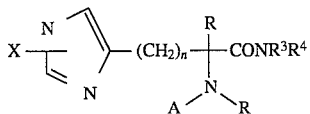

wherein:
n=1 or 2;
A=COR$^2$, CO$_2$R$^2$, CONHR$^2$, CSR$^2$, C(S)OR$^2$, C(S)NHR$^2$, or SO$_2$R$^2$ with R$^2$ as defined below;
R=independently H or Me;
R$^2$=alkyl, (CH$_2$)$_m$-cycloalkyl, (CH$_2$)$_m$-aryl, or (CH$_2$)$_m$-heteroaryl with m=0, 1, 2, or 3;
R$^3$ and R$^4$=independently (CH$_2$)$_x$-R$^7$, with x=2–5 and R$^7$ as defined below,

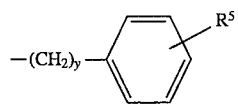

or (CH$_2$)$_n$CONH-R$^6$ with y=1–5 and n as defined above and with R$^5$ and R$^6$ as defined below, or R$^3$ and R$^4$ are connected together to form a ring of the following type:

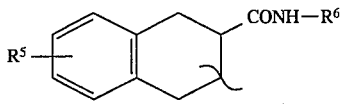

with R$^5$ and R$^6$ as defined below;
R$^5$=R$^2$, OR$^2$, or SR$^2$ with R$^2$ as defined above;
R$^6$=(CH$_2$)$_n$R$^5$, (CH$_2$)$_n$CO$_2$R$^2$, (CH$_2$)$_n$CONHR$^2$, (CH$_2$)$_n$CONH(CH$_2$)$_{n+1}$R$^5$, or CH(COR$^8$)(CH$_2$)$_n$R$^5$, with n, R$^2$, and R$^5$ as defined above and R$^8$ as defined below;
R$^7$=(CH$_2$)$_m$-cycloalkyl, (CH$_2$)$_m$-aryl, (CH$_2$)$_m$-heteroaryl, O(CH$_2$)$_m$-cycloalkyl, O(CH$_2$)$_m$-aryl, or O(CH$_2$)$_m$-heteroaryl with m=0, 1, 2, or 3;
R$^8$=OH, O-alkyl, NH$_2$, or NH-alkyl; and
X=H, Me, (CH$_2$)$_n$CO$_2$R$^9$, or (CH$_2$)$_n$P(O)(OR$^9$)$_2$, with R$^9$=H or alkyl; or a pharmaceutically acceptable salt thereof.

2. An inhibitor according to claim 1 which is a compound of Formula II:

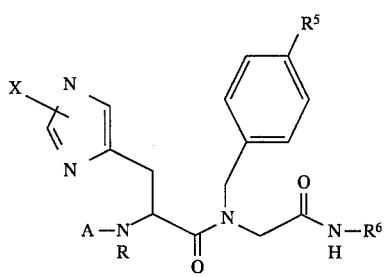

wherein:
A is limited to CO$_2$R$^2$, CONHR$^2$, C(S)OR$^2$, or C(S)NHR$^2$ with R$^2$ as defined below;
R=H or Me;
R$^2$ is limited to alkyl, (CH$_2$)$_m$-cycloalkyl, (CH$_2$)$_m$-aryl, or (CH$_2$)$_m$-heteroaryl, with m=0, 1, 2, or 3;

R$^5$ is limited to (CH$_2$)$_m$-aryl, O-(CH$_2$)$_m$-aryl, or O-(CH$_2$)$_m$-heteroaryl with m as defined above;
R$^6$ is limited to (CH$_2$)$_n$-R$^5$, (CH$_2$)$_n$CO$_2$R$^2$, or CH$_2$CONHR$^2$, with n=1 or 2, and with R$^5$ and R$^2$ as defined above; and
X is limited to H or Me;
or a pharmaceutically acceptable salt thereof.

3. An inhibitor according to claim 1 which is a compound of Formula III:

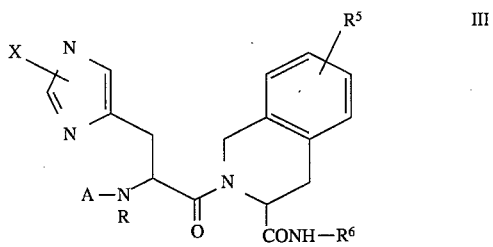

wherein:
A is limited to CO$_2$R$^2$, CONHR$^2$, C(S)OR$^2$, or C(S)NHR$^2$ with R$^2$ as defined below;
R=H or Me;
R$^2$ is limited to alkyl, (CH$_2$)$_m$-cycloalkyl, (CH$_2$)$_m$-aryl, or (CH$_2$)$_m$-heteroaryl, with m=0, 1, 2, or 3;
R$^5$ is limited to (CH$_2$)$_m$-aryl, O-(CH$_2$)$_m$-aryl, or O-(CH$_2$)$_m$-heteroaryl with m as defined above;
R$^6$ is limited to (CH$_2$)$_n$-R$^5$, (CH$_2$)$_n$CO$_2$R$^2$, or CH$_2$CONHR$^2$, with n=1 or 2, and with R$^5$ and R$^2$ as defined above; and
X is limited to H or Me;
or a pharmaceutically acceptable salt thereof.

4. An inhibitor according to claim 1 which is a compound of Formula II:

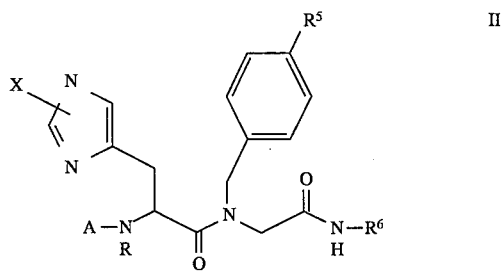

wherein:
A is further limited to CO$_2$R$^2$ or CONHR$^2$, with R$^2$ as defined below;
R is limited to H;
R$^2$ is further limited to alkyl, or (CH$_2$)$_m$-aryl with m=0, 1, 2, or 3;
R$^5$ is further limited to (CH$_2$)$_m$-aryl or O-(CH$_2$)$_m$-aryl with m as defined above;
R$^6$ is limited to (CH$_2$)$_n$-R$^5$ or (CH$_2$)$_n$CONHR$^2$, with n=1 or 2, and with R$^5$ and R$^2$ as defined above; and
X is limited to H or Me;
or a pharmaceutically acceptable salt thereof.

5. An inhibitor according to claim 1 which is a compound of Formula III:

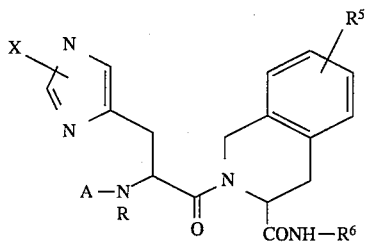

wherein:

A is further limited to $CO_2R^2$ or $CONHR^2$, with $R^2$ as defined below;

R is limited to H;

$R^2$ is further limited to alkyl, or $(CH_2)_m$-aryl with m=0, 1, 2, or 3;

$R^5$ is further limited to $(CH_2)_m$-aryl or $O-(CH_2)_m$-aryl with m as defined above;

$R^6$ is limited to $CH_2$-$R^5$ or $CH_2CONHR^2$, with $R^5$ and $R^2$ as defined above; and X is limited to H or Me;

or a pharmaceutically acceptable salt thereof.

6. An inhibitor of claim 1 which is: N-[(Phenylmethoxy)carbonyl]-L-histidyl-N-[2-(phenylmethoxy)ethyl]-$N^2$-[[4-(phenylmethoxy)phenyl]methyl]glycinamide.

7. An inhibitor of claim 1 which is: N-[(Phenylmethoxy)carbonyl]-L-histidyl-$N^2$-[(1,1'-biphenyl)-4-ylmethyl]-N-[2-(phenylmethoxy)ethyl]glycinamide.

8. An inhibitor of claim 1 which is: N-[N-[N-[(Phenylmethoxy)carbonyl]-L-histidyl]-N-[[4-(phenylmethoxy)phenyl]methyl]glycyl]glycine phenylmethyl ester.

9. An inhibitor of claim 1 which is: N-[(Phenylmethoxy)carbonyl]-L-histidyl-N-(4-phenylbutyl)-$N^2$-[[4-(phenylmethoxy)phenyl]methyl]glycinamide.

10. An inhibitor of claim 1 which is: N-[(Phenylmethoxy)carbonyl]-L-histidyl-N-(3-phenoxypropyl)-$N^2$-[[4-(phenylmethoxy)phenyl]methyl]glycinamide.

11. An inhibitor of claim 1 which is: (S)-[1-(1H-Imidazol-3-ylmethyl)-2-oxo-2-[[2-(phenylmethoxy)ethyl][[4-(phenylmethoxy)phenyl]methyl]amino]ethyl]-carbamic acid, phenylmethyl ester.

12. An inhibitor of claim 1 which is: [1-(1H-Imidazol-4-ylmethyl)-2-oxo-2-[1,2,3,4-tetrohydro-7-(phenylmethoxy)-3-[[[2-phenylmethoxy)ethyl]amino]carbonyl]-2-isoquinolinyl]ethyl]carbamic acid, phenylmethyl ester.

13. A method of treating ras-related tissue proliferative diseases comprising administering to a host suffering therefrom a therapeutically effective amount of an inhibitor according to claim 1 in unit dosage form.

14. A pharmaceutical composition adapted for administration as an antiproliferative agent comprising a therapeutically effective amount of an inhibitor according to claim 1 in admixture with a pharmaceutically acceptable excipient, diluent or carrier.

15. A method of treating ras-related cancer comprising administering to a host suffering therefrom a therapeutically effective amount of an inhibitor according to claim 1 in unit dosage form.

16. A pharmaceutical composition adapted for administration as an anticancer agent comprising a therapeutically effective amount of an inhibitor according to claim 1 in admixture with a pharmaceutically acceptable excipient, diluent or carrier.

17. A method of treating restenosis comprising administering to a host suffering therefrom a therapeutically effective amount of an inhibitor according to claim 1 in unit dosage form.

18. A pharmaceutical composition adapted for administration as a restenosis inhibiting agent comprising a therapeutically effective amount of an inhibitor according to claim 1 in admixture with a pharmaceutically acceptable excipient, diluent or carrier.

19. A solution synthesis method of preparing an inhibitor according to claim 1, or a pharmaceutically acceptable salt thereof, comprising the preparation of secondary amines and N-substituted amino acids by hydride reduction of an imine formed between an aldehyde and an amine or an amino acid, followed by reaction with an N-substituted histidine or homohistidine derivative, a carbodiimide and 1-hydroxybenzotriazole.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Xaa  Tyr  Lys  Cys  Val  Ile  Met
    1